(12) United States Patent
Haraldsson et al.

(10) Patent No.: US 8,053,430 B2
(45) Date of Patent: Nov. 8, 2011

(54) TREATMENT OF RENAL CELL CARCINOMA

(76) Inventors: Börje Haraldsson, Landvetter (SE); Ulf Nilsson, Gothenburg (SE); Lisa Buvall, Lerum (SE); Jenny Nyström, Gothenburg (SE)

( * ) Notice: Subject to any disclaimer, the term of this patent is extended or adjusted under 35 U.S.C. 154(b) by 0 days.

(21) Appl. No.: 12/586,849

(22) Filed: Sep. 29, 2009

(65) Prior Publication Data

US 2010/0152243 A1     Jun. 17, 2010

Related U.S. Application Data

(60) Provisional application No. 61/195,312, filed on Oct. 6, 2008.

(51) Int. Cl.
*A61K 31/33* (2006.01)

(52) U.S. Cl. .................................................. 514/183

(58) Field of Classification Search .............. 514/183
See application file for complete search history.

(56) References Cited

U.S. PATENT DOCUMENTS

| 6,403,373 | B1 | 6/2002 | Scanlan et al. |
| 6,440,663 | B1 | 8/2002 | Scanlan et al. |
| 2005/0261178 | A1 | 11/2005 | Warnaar et al. |
| 2006/0134708 | A1 | 6/2006 | Yang |

FOREIGN PATENT DOCUMENTS

| CN | 1359941 A | 7/2002 |
| EP | 0 160 250 | 6/1985 |
| EP | 1 712 234 A1 | 10/2006 |
| JP | 2001288110 A | 10/2001 |
| RU | 2188026 C | 8/2002 |
| WO | WO 2004/075887 A1 | 9/2004 |
| WO | WO 2007/044015 A1 | 4/2007 |
| WO | WO 2007/059082 A1 | 5/2007 |

OTHER PUBLICATIONS

Rapior et al 'Intoxication by *Cortinarius orellanus*: Detection and assay of orellanine in biological fluids and renal biopsies' Mycopathologia, vol. 108, p. 155-161, 1989.*
Atkins, MB et al., 2007, Innovations and Challenges in Renal Cell Carcinoma: Summary Statement from the Second Cambridge Conference, Clin. Cancer Res. 13:667-670.
Garcia, JA et al., 2007, Recent progress in the management of advanced renal cell carcinoma, CA Cancer J. Clin. 57: 112-25.
Sutphin, PD et al., 2007, Targeting the loss of the von Hippel-Lindau Tumor Suppressor Gene in Renal Carcinoma Cells, Cancer Res. 67: 5896-5905.

* cited by examiner

*Primary Examiner* — Brandon Fetterolf
*Assistant Examiner* — Christopher R Stone
(74) *Attorney, Agent, or Firm* — Lynn E. Barber

(57) ABSTRACT

Methods are provided of treating renal cancer by administration of certain 3,3',4,4'-tetrahydroxy-2,2'-bipyridine-N,N'-dioxide compounds, especially 3,3',4,4'-tetrahydroxy-2,2'-bipyridine-N,N'-dioxide (Orellanine), using particular administration protocols and dosing regimens, as well as pharmaceutical compositions suitable for use in the treatment methods that are provided.

14 Claims, 8 Drawing Sheets

Figure 2  786-O cells after one week of orellanine incubation

TREATMENT OF RENAL CELL CARCINOMA

CROSS-REFERENCE TO RELATED APPLICATIONS

This application claims priority from U.S. provisional application Ser. No. 61/195,312 filed Oct. 6, 2008.

FIELD OF THE INVENTION

The present invention relates generally to cancer treatment. More specifically this invention relates to the use of 3,3',4,4'-tetrahydroxy-2,2'-bipyridine-N,N-dioxides, especially 3,3',4,4'-tetrahydroxy-2,2'-bipyridine-N,N'-dioxide (Orellanine), for the treatment of renal cancer, particularly renal cell carcinoma originating from renal proximal tubular cells.

BACKGROUND OF THE INVENTION

Cancer appears in more than 100 different forms that affect nearly every part of the body. Throughout life, healthy cells in the body divide, grow, and replace themselves in a controlled fashion. Cancer results when the genes dictating this cellular division malfunction and cells begin to multiply and grow out of control. A mass or clump of these abnormal cells is called a tumor. Not all tumors are cancerous. Benign tumors, such as moles, stop growing and do not spread to other parts of the body. Cancerous or malignant tumors, however, continue to grow and smother healthy cells, interfere with body functions, and draw nutrients away from body tissues. Malignant tumors can spread to other parts of the body through a process called metastasis. Cells from the "mother tumor" detach, migrate via the blood or lymphatic vessels or within the chest, abdomen or pelvis, depending on the tumor, and they eventually form new tumors elsewhere in the body.

Cancer in the kidney constitutes about 3% of all solid tumors. About 85% of renal tumors are classified as renal cell carcinoma (RCC) Approximately 80% of diagnosed RCC originate from the epithelial cells lining the proximal parts of the kidneys' urine-forming ducts, the tubuli. Due to its appearance under the microscope, this cancer type is known as either renal clear cell carcinoma (RCCC, 65%) or renal papillary cell carcinoma (RPCC, 15%). While RCCC and RPCC constitute 80% of diagnosed RCC, they are responsible for closer to 100% of the deaths from renal cell carcinoma.

The most important factor in predicting prognosis is the stage. The stage describes the cancer's size and how deeply it has spread beyond the kidney. The Staging System of the American Joint Committee on Cancer (AJCC) is known as the TNM system. The letter T followed by a number from 1 to 3 describes the tumor's size and spread to nearby tissues. Higher T numbers indicate a larger tumor and/or more extensive spread to tissues near the kidney. The letter N followed by a number from 0 to 2 indicates whether the cancer has spread to lymph nodes near the kidney and, if so, how many are affected. The letter M followed by a 0 or 1 indicates whether or not the cancer has spread to distant organs.

Stage I: The tumor is 7 cm (about 2¾ inches) or smaller, and limited to the kidney. There is no spread to lymph nodes or distant organs.

Stage II: The tumor is larger than 7.0 cm but still limited to the kidney. There is no spread to lymph nodes or distant organs.

Stage III: Includes tumors of any size, with or without spread to fatty tissue around the kidney, with or without spread into the large veins leading from the kidney to the heart, with spread to one nearby lymph node, but without spread to distant lymph nodes or other organs. Stage III also includes tumors with spread to fatty tissue around the kidney and/or spread into the large veins leading from the kidney to the heart, that have not spread to any lymph nodes or other organs.

Stage IV: This stage includes any cancers that have spread directly through the fatty tissue and the fascia ligament-like tissue that surrounds the kidney. Stage 1V also includes any cancer that has spread to more than one lymph node near the kidney, to any lymph node not near the kidney, or to any other organs such as the lungs, bone, or brain.

Detailed definitions of renal cell cancer, T, N, M categories, and stage groupings:

Primary Tumor (T):
TX: Primary tumor cannot be assessed
T0: No evidence of primary tumor
T1: Tumor 7 cm or less, limited to kidney
T2: Tumor greater than 7 cm, limited to kidney
T3: Tumor extends into major veins/adrenal/perinephric tissue; not beyond Gerota's fascia
T3a: Tumor invades adrenal/perinephric fat
T3b: Tumor extends into renal vein(s) or vena cava below diaphragm
T3c: Tumor extends into vena cava above diaphragm
T4: Tumor invades beyond Gerota's fascia
N—Regional Lymph Nodes
NX: Regional nodes cannot be assessed
N0: No regional lymph node metastasis
N1: Metastasis in a single regional lymph node
N2: Metastasis in more than one regional lymph node
M—Distant Metastasis
MX: Distant metastasis cannot be assessed
M0: No distant metastasis
M1: Distant metastasis As a rule of thumb, cancer in stage I or II is treated by surgical removal of the afflicted kidney and the prognosis for recovery is good. In contrast, renal cancers of stage III or IV are associated with very low survival rates, and the National Cancer Institute states on its website that "Virtually no patients with renal cell cancer in stage 1V can be cured."

The National Cancer Institute estimates 49,096 new cases of renal cancer to be diagnosed in the U.S. in 2009 ($16/10^5$ citizens) with 11,033 ensuing deaths ($3,6/10^5$ citizens). the corresponding numbers for the European Union (2006) are 65,051 diagnoses ($7,8/10^5$ citizens) and 27,326 deaths ($3,3/10^5$ citizens) (*European Cancer Observatory*: http://eu-cancer.iarc.fr/cancer-19-kidney.html,en). Worldwide estimates (2006) are 209,000 diagnosed cases ($3,2/10^5$ citizens) and 102,000 deaths ($1,6/10^5$ citizens) (Gupta et al. Cancer Treat. Rev. 34, 193-205; 2008). The seemingly higher incidence in the U.S. is due to the fact that the NCI co-reports cancer of the renal pelvis (which is relatively easy to treat) with renal cell carcinomas. The lower global incidence and death rates are likely due, at least in part, to under diagnosis in large areas of the Third World.

The main problem with conventional art is that, as mentioned above, the outcome for any one patient diagnosed with renal cancer is dictated largely by the timing of the diagnosis. If the disease is diagnosed before the tumor has spread outside the kidney the chance for survival is good, otherwise most patients die from the disease. The main reason for this is that renal cell carcinoma is refractory to all conventional therapy with cytostatic and/or cytotoxic drugs, such as cisplatin, carboplatin, docetaxel, paclitaxel, fluorouracil, capecitabine, gemcitabine, irinotecan, topotecan, etoposide, mitomycin, gefitinib, vincristine, vinblastine, doxorubicin, cyclophosphamide, celecoxib, rofecoxib, and/or valdecoxib.

Various solutions are described in the prior art. Conventional chemotherapy against renal cell carcinoma is generally contraindicated due to poor effectiveness and extensive side effects. Alternative treatment modalities have thus been sought, and they can be divided into several categories:

1) Antiangiogenesis. In this strategy the tumor is denied nutrients and oxygen through inhibition of formation of the blood vessels necessary for supplying the tumor tissue. This can be achieved in several ways: 1a) inhibition of circulating growth factors, such as VEGF, PDGF, and PlGF, by treatment with antibodies directed against these growth factors; 1b) blocking of receptors for vascular growth factors on target cells with antibodies directed against the receptors; and 1c) treatment with smaller molecules that interfere with receptor function in such a way that binding of a vascular growth factor to its receptor fails to elicit the physiological angiogenetic effect.

2) Immunomodulatory treatment. This strategy attempts to stimulate the endogenous immune system to recognize the tumor cells as alien and start fighting them. Immune stimulation as treatment against renal cancer takes two main routes: 2a) treatment with interleukin 2 (IL-2); and 2b) interferon alpha (IFNα) therapy.

All of the alternative treatment strategies mentioned above significantly improve the life span of some patients with renal cancer in an advanced stage. However, the effect is in the order of only a few months, and the treatment is associated with numerous serious side-effects. Very often the tumor adapts to the treatment which then has to be discontinued. This is followed by an accelerated rate of tumor growth. Recent strategies for the treatment of renal cancer have been reviewed by Garcia et al. ("Recent progress in the management of advanced renal cell carcinoma." *CA Cancer. J. Clin.* 57(2): 112-25 (2007)) and by Atkins et al. ("Innovations and challenges in renal cell carcinoma: summary statement from the Second Cambridge Conference." *Clin. Cancer. Res.* 13(2 Pt 2): 667s-670s (2007)).

A review of the literature indicated that many of the therapeutic approaches originate from the identification of more or less specific cancer markers and the use of these markers to elicit a host immune response directed against the invading tumor tissue. Thus, US2006134708 discloses several molecular markers of kidney and urothelial cancer, namely IGFBP-3 (insulin-like growth factor-binding protein 3), ANGPTL4 (angiopoietin-like 4) and ceruloplasmin, as well as monoclonal antibodies directed against said markers, for diagnostic purposes. The use on the peptide and nucleic acid level of antisense compounds directed against the disclosed markers is described. Also, the use of monoclonal antibodies against the markers, the antibodies being conjugated to cytotoxic agents, is contemplated as a therapeutic embodiment associated with less severe side-effects of the cytotoxic agents due to the targeting afforded by the antibody (aka the "magic bullet" concept). A similar strategy, based on different tumor-associated antigens, is adopted in CN1359941.

U.S. Pat. No. 6,403,373 discloses nucleic acid molecules associated with colon, renal and stomach cancer, the peptide products of which gives rise to antibody production in a host. Use of the peptides in a vaccine approach is contemplated. EP0160250 discloses monoclonal antibodies for the diagnosis of renal carcinoma, and mentions the possibility of conjugating these to various cytotoxic agents.

WO2007059082 discloses the occurrence of the antigen TIM-1 (T cell, immunoglobulin or mucin domain 1), which is associated with cellular proliferation, in ovarian and renal cancer. The use of antibodies raised against TIM-1 for the treatment of ovarian and renal cancer is taught, as is the conjugation of therapeutic agents (toxins, radioisotopes or chemotherapeutic agents) to said antibodies as a means of targeted killing of tumor cells.

U.S. Pat. No. 6,440,663 discloses a number of genes expressed by renal cancer cells, the products of which lead to antibody production in the host. Various approaches to eliciting or augmenting an immune response in the host towards the tissue expressing the disclosed genes are described, including the raising of cytotoxic T-cells and transfection of host cells with the disclosed genes or fragments thereof, followed by reintroduction of said cells into the host.

US 2005261178 discloses the co-administration of a monoclonal antibody (G250), directed against an antigen (carbonic anhydrase IX) expressed on the majority of renal cancers, and the cytokines Interleukin-2 or Interferon-α. The cytokines were administered in lower doses than those used when treating with cytokines only. Stabilization of the disease for 22 weeks or longer, or an "objective response", was achieved in about 30% of the patients in a group suffering from advanced renal cancer.

Other approaches are based on the use of known therapeutic substances in new treatment regimes. For example, WO2007044015 discloses the use of previously known dimethane sulfonate compounds, in particular NSC-281612, according to a new administration protocol in order to treat renal cancer. When tested on xenografts in nude mice, administration of NSC-281612 led, in some cases, to apparently complete eradication of the tumor mass.

JP2001288110 discloses the conjugation of interferon-α to polyethylene glycol (PEG) in an attempt to increase circulating half-life and decrease the smallest therapeutically effective dose.

RU2188026 discloses a polychemotherapy regimen with vincristine, adriamycin and depo-provera. This is claimed to increase the relapse-free period and diminish metastasis formation.

Finally, in a few instances, suggested therapy is founded on new original substances. Thus, WO2004075887 discloses the use of 1-(2-chloroethyl)-1-nitroso-3-(2-hydroxyethyl)urea (HECNU) for the treatment of many cancer types, including renal cancer. The main feature of HECNU is an improved water solubility compared to the previously known corresponding compound, Bis-(2-chlorethyl)-1-nitroso-urea (BCNU).

EP1712234 discloses the use of 4-pyridylmethyl-phthalazine derivatives as VEGF receptor inhibitors in the treatment of renal cancer, especially for the inhibition of metastatic growth. It was found that co-administration of the 4-pyridyl-methyl-phthalazine derivatives with either of a plurality of conventional chemotherapeutic agents had a synergistic effect, even though the tumor cells are refractory to the chemotherapy alone. Further, combination therapy was associated with noticeably smaller side-effects.

Suthpin et al. ("Targeting the Loss of the von Hippel-Lindau Tumor Suppressor Gene in Renal Carcinoma Cells", Cancer. Res. 67(12), 5896-5905 (2007)) studied the selective effect of Chromomycin A3 on renal cancers not expressing the VHL gene (this tumor-suppressing gene is absent in about 70% of all renal clear cell cancers). Chromomycin A3 significantly retarded tumor growth in xenografted nude mice without affecting normal renal tissue, expressing the VHL gene.

The invention herein utilizes Orellanine (Formula I), which is a selective renal toxin occurring in relatively large amounts in several fungal species of the *Cortinarius* family. Intoxication with orellanine after confusion of *Cortinarius* fungi with edible mushrooms occurs regularly throughout Europe, Russia and North America. After ingestion of orellanine-containing fungi, there is a period of a few days up to 3 weeks with no symptoms or only mild, influenza-like symptoms. The next phase, when medical help is generally sought, is characterized by uremia due to acute renal failure. Despite many descriptions of orellanine poisoning in the scientific literature, no other effects of orellanine have been reported apart from the renal toxicity just mentioned (Danel V C, Saviuc P F, Garon D: Main features of *Cortinarius* spp. poisoning: a literature review. *Toxicon* 39, 1053-1060 (2001).). This selectivity most likely resides with the fact that orellanine is taken up specifically by one cell type, i.e., the tubular epithelial cells, particularly the proximal tubular epithelial cells (Prast H, Pfaller W: Toxic properties of the mushroom *Cortinarius orellanus* (Fries) II. Impairment of renal function in rats. *Arch Toxicol* 62, 89-96 (1988).). The toxin mechanism of Orellanine has not been elucidated, and no treatment is available except maintenance dialysis while waiting to see whether the kidneys will recover or not. The final outcome is critically dependent on the amount of toxin ingested, and, as a rule of thumb, ingestion of one fungus gives temporary problems, two fungi leads to permanent loss of part of the renal function whereas three or more fungi results in total loss of renal function and lifelong need for dialysis or renal replacement therapy.

The applicants have recently published a first study of the mode of action of Orellanine in healthy rats (Nilsson U A et al. The fungal nephrotoxin orellanine simultaneously increases oxidative stress and down-regulates cellular defenses. *Free Rad. Biol. Med.* 44:1562-9 (2008).). This study shows increased oxidative stress in cortical renal tissue along with dramatically decreased expression of several key antioxidant genes. During this work it was realized that the seemingly absolute specificity of Orellanine for renal tubular epithelial cells could theoretically be extended to encompass these cells also after their transformation into cancer cells. If proven true, such a hypothesis would mean that Orellanine is a powerful weapon against renal cancer of epithelial origin, with curative potential even in advanced stages and with metastases in other tissues.

Pursuing this hypothesis, it was surprisingly discovered that Orellanine was indeed taken up also in human renal cancer cells, and killed them with great efficiency whether they were derived from a primary tumor or from metastatic tumor tissue. The cell death progressed for many days after transient exposure to Orellanine, indicating that the toxin was actively taken up and retained by the cells.

SUMMARY OF THE INVENTION

A primary object of the present invention is to provide a method for treating renal cancer originating from epithelial cells, which method involves administering to a mammal in need thereof at least one compound according to Formula I.

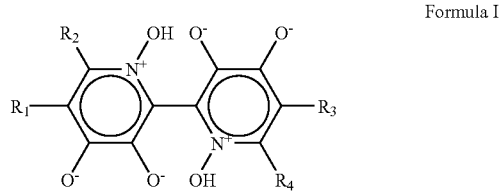

Formula I

Another object of the present invention is to provide a pharmaceutical composition comprising at least one compound according to Formula I, optionally comprising other agents with anti-cancer activity, as well as carriers and any other excipients needed to optimize the effectiveness of the composition.

Yet another object is to provide a kit that contains the above composition, in one or more separate compartments, along with diluents and/or solvents as needed, such that the composition easily can be made ready for use by the treating physician or nurse.

Upon reading of the description and the examples, other objects and advantages of the present invention will become obvious to the person with normal skills in this field, and these objects and advantages are intended to fall within the scope of the present invention.

For ERK 1/2 and p38, the ratios of phosphorylated (f) to total protein should be compared. Cleaved caspase 3 should be compared to the loading control, beta actin.

Figure 7:
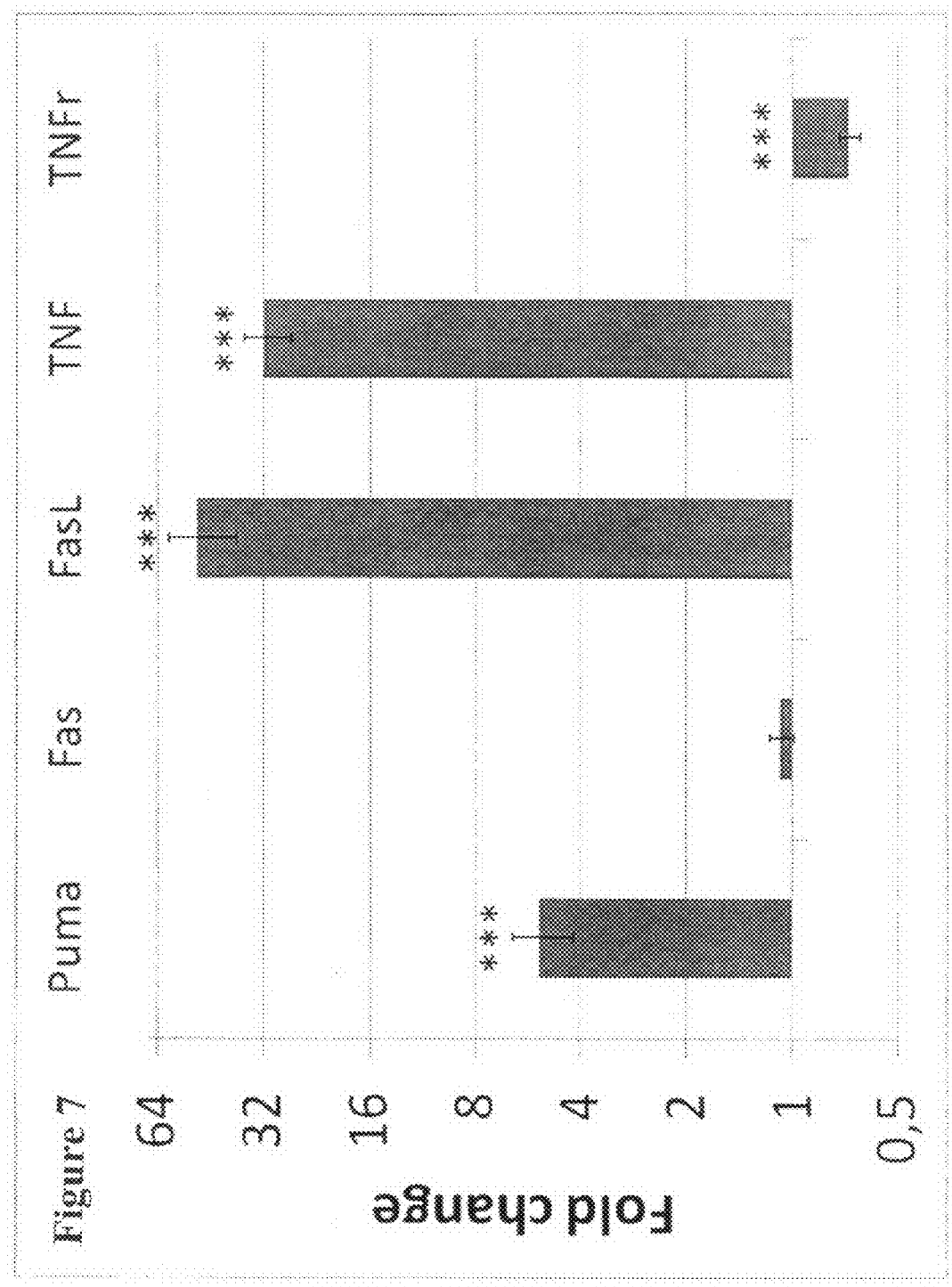

FIG. 7: Induction of apoptosis by orellanine in renal carcinoma cells (SKRC-52): mRNA effects. RT-PCR analysis of mRNA expression of the apoptosis mediators PUMA, Fas ligand (FasL) and Tumor Necrosis Factor alpha (TNF) revealed a dramatic up-regulation in all three cases. Only small changes in the expression of receptor mRNA was noted. Cells are compared to control cells incubated without orellanine.

Figure 8:
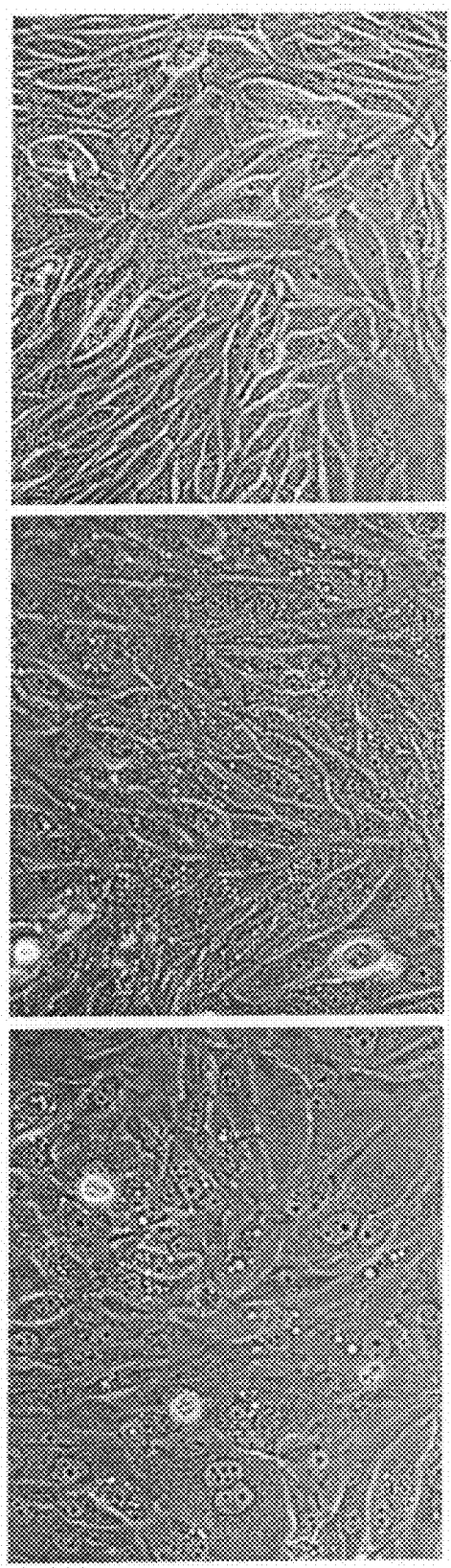

FIG. 8: Apoptosis in human clear cell cancer (SKRC52) during incubation with Orellanine. Typical signs of apoptosis, vacuolization and cell shrinkage, are evident already after 4 h incubation, and are further aggravated after 24 h.

DETAILED DESCRIPTION OF THE INVENTION AND PREFERRED EMBODIMENTS THEREOF

The present invention provides pharmaceutical compositions comprising pyridine-N-oxide and bipyridine-N,N-dioxide compounds and methods of treating renal cancer by administering the pharmaceutical compositions to a patient suffering from or susceptible to renal cancer. The invention herein also includes a kit for treating a patient suffering from or susceptible to renal cancer.

The present invention provides a method for treating a patient suffering from or susceptible to renal cell carcinoma in which the method comprises the step of administering to the patient a compound according to Formula I as defined previously, a pharmaceutically acceptable salt thereof or a pharmaceutical composition comprising said compound.

Compounds of Formula I administered to a patient include those compounds in which R1, R2, R3 and/or R4 do not substantially interfere with the cytotoxicity of orellanine (R1=R2=R3=R4=hydrogen). Thus, R1, R2, R3 and/or R4 include, but are not limited to, hydrogen, amino, mercapto, carboxy, phosphate and halo, including fluoro, chloro, and bromo, $C_1$-$C_6$ alkyl, $C_1$-$C_6$ alkenyl, $C_1$-$C_6$ alkynyl, $C_1$-$C_6$ alkanol, $C_1$-$C_6$ alkenol, $C_1$-$C_6$ alkoxy, $C_1$-$C_6$ alkenoxy, each of which may be further substituted with groups including but not limited to amino, mercapto, carboxy, phosphate and halo, including fluoro, chloro, and bromo.

In one embodiment of the methods according to the present invention of treating patients suffering from or susceptible to renal cancer, the compound of Formula I administered to the patient is a pharmaceutically acceptable salt, hydrate, or solvate. As used herein, a pharmaceutically acceptable salt is an acid or base salt that is generally considered in the art to be suitable for use in contact with the tissues of human beings or animals without excessive toxicity, irritation, allergic response, or other problems or complications. Such salts include mineral and organic acid salts of basic residues, such as amines. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0-4, and the like.

In the methods of treating renal cancer provided herein, the compound of Formula I can be administered in a single dose, in a series of daily doses or in an intermittent dosing format (e.g., a plurality of doses or dose sequences administered between 1 and about 30 days apart, between 1 and about 14 days apart or between 1 and about 7 days apart). In certain methods, the administration protocol and compound of Formula I are selected to provide at least a 50% reduction in tumor size, or more preferably at least a 75%, 90%, or 95% reduction in tumor size after completion of the administration protocol, while in certain other methods, selection of the administration protocol and compound of Formula I result in a 95% reduction in tumor size, a 99% reduction in tumor size or a substantially complete elimination of the tumor. In those methods of treatment comprising a single dose administration protocol, a single dose of between about 1 mg/kg and about 100 mg/kg of a compound according to the Formula (I) or an equivalent molar amount of a pharmaceutically acceptable salt thereof is administered to the patient, while a preferred single dose comprises between about 2 mg/kg and about 25 mg/kg, most preferably between about 5 mg/kg and about 15 mg/kg of a compound of Formula I or an equivalent molar amount of a pharmaceutically acceptable salt thereof is administered to the patient.

In certain other therapeutic methods of treating renal cancer, a compound of Formula I, or a pharmaceutically acceptable salt thereof is administered to the patient suffering from or susceptible to renal cancer in two or more doses. Typically the doses are administered daily or intermittently (e.g., with at least one non-administration day separating sequential doses). In certain methods in which the compound of Formula I, or a pharmaceutically acceptable salt thereof is administered in a plurality of doses, each dose comprises between about 0.5 mg/kg and about 10 mg/kg of the compound, or more preferably, each dose comprises between about 1 mg/kg and about 5 mg/kg, or most preferably about 2 mg/kg of the compound or salt of Formula I.

In certain methods in which sequential doses are administered intermittently, the sequential doses are administered between two and seven days apart, in yet other methods comprising intermittent administration of the compound or salt of Formula I, the compound is administered to the patient in three, four, five or six or more doses and wherein each dose is administered between three and five days apart, in yet other methods, the patient is administered four, five, or six or more doses administered between three and four days apart, wherein each dose comprises between about 1 mg/kg to about 20 mg/kg of a compound of Formula I or a pharmaceutically acceptable salt thereof, preferably 2-10 mg/kg and most preferably about 5 mg/kg. In certain other therapeutic methods of treating renal cancer, the patient is administered a daily dose of a compound of Formula I, or a pharmaceutically acceptable salt thereof, for at least two days. Typical daily doses administered to patients are between 0.1 and 10 mg/kg, preferably between 1 and 5 mg/kg, and most preferably about 2 mg/kg. Therapeutic protocols typically comprise daily administration of the compound of Formula I, or a pharmaceutically acceptable salt thereof, between 5 and about 30 days, or preferably between 10 and 20 days, or most preferably about 14 days.

In certain instances, it may be desirable to conduct a plurality of intermittent administration protocols, daily administration protocols, or a combination thereof, as described above, in combination with rest and/or recovery periods. Thus, in certain instances, it may be desirable to administer a compound of Formula I, or a pharmaceutically acceptable salt thereof, according to a daily or intermittent administration method provided herein, measure the tumor response to the therapy, and then conduct subsequent daily or intermittent administration therapies as necessary to eliminate or further reduce the size of the renal cancer tumors. Such administration strategies are well known to the person with normal skills in the field of oncology.

In one particularly preferred embodiment of the present invention a patient suffering from renal cell carcinoma is treated with the substance according to Formula I of the present invention by daily injections of about 0.5-5 mg orellanine/kg b.w., most preferably about 2 mg orellanine/kg b.w., for about 7-21 consecutive days, most preferably about 14 consecutive days. One to 5 hours after each daily injection of a compound according to Formula I, most preferably about 2 hours after such injection, the patient is subjected to hemodialysis for 1-5 h, most preferably about 2 h, in order to eliminate any compound according to Formula I that has not been taken up into tumor tissue and thereby minimize any undesired side effects that might occur in the extracellular space.

The preferred doses and dose regimes described above are based on a human being weighing 70 kg and suffering from renal cell carcinoma with a tumor burden of about 1 kg. However, as is readily known to the worker with normal skills in the field of cancer medicine, such preferred doses and dose regimes are governed to a large extent by patient characteristics such as age, sex, weight, general condition and, above all, the individual patient's tumor burden and response to the treatment. As always, the ultimate responsibility for choosing the proper dose and treatment strategy lies with the physician in charge of the patient.

The invention provides methods of treating patients suffering from or susceptible to renal cell carcinoma. In certain methods, the tumor to be treated is localized to one or both of the patient's kidneys. In certain other methods, the renal cell carcinoma has metastasized, e.g., at least one renal cell carcinoma tumor is present in at least one non-kidney tissue. Typically the methods provided herein are suitable for use in the treatment of patients suffering from or susceptible to renal cell carcinoma tumors which are present in the kidneys, in non-kidney tissues, or in a combination thereof. In a preferred embodiment, the tumors are present in non-kidney tissues or in a combination of kidney and non-kidney tissues. The methods of treatment provided by the instant invention contemplate any administration pathway capable of providing a therapeutically effective dose of a compound of Formula I to the vicinity of the tumor. In certain preferred methods of treatment provided herein, the compound of Formula I, or a pharmaceutical composition comprising same is administered intravenously, subcutaneously, or intraperitoneally. Typically the compound of Formula I, or a pharmaceutical composition comprising same is administered intravenously.

In another aspect, the invention provides a pharmaceutical composition comprising at least one pharmaceutically acceptable carrier and a compound according to the Formula (I), wherein R1, R2, R3 and/or R4 do not substantially interfere with the cytotoxicity of orellanine (R1=R2=R3=R4=hydrogen). Thus, R1, R2, R3 and/or R4 are exemplified by, but not limited to, hydrogen, amino, mercapto, carboxy, phosphate and halo, including fluoro, chloro, and bromo, $C_1$-$C_6$ alkyl, $C_1$-$C_6$ alkenyl, $C_1$-$C_6$ alkynyl, $C_1$-$C_6$ alkanol, $C_1$-$C_6$ alkenol, $C_1$-$C_6$ alkoxy, $C_1$-$C_6$ alkenoxy, each of which may be further substituted with groups including but not limited to amino, mercapto, carboxy, phosphate and halo, including fluoro, chloro, and bromo.

In certain other pharmaceutical compositions, the compound of Formula I is incorporated into the composition as a pharmaceutically acceptable salt, hydrate, or solvate. As used herein, a pharmaceutically acceptable salt is an acid or base salt that is generally considered in the art to be suitable for use in contact with the tissues of human beings or animals without excessive toxicity, irritation, allergic response, or other problem or complication. Such salts include mineral and organic acid salts of basic residues such as amines. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0-4, and the like.

The pharmaceutical compositions provided by the instant invention are suitable for use in any administration pathway contemplated by the methods of treatment in which the compositions will be used. In the methods of the invention, compounds of the invention according to Formula I and pharmaceutical compositions thereof may be administered to a subject by a variety of routes including parenteral (including intravenous, subcutaneous, intramuscular and intradermal), topical (including buccal, sublingual), oral, nasal and the like. In certain preferred pharmaceutical compositions provided herein, the pharmaceutical composition is formulated for administration by intravenous, subcutaneous, or intraperitoneal injection. Typically the pharmaceutical composition is formulated for administered by intravenous injection.

In certain parenteral administration routes, the pharmaceutical composition is a sterile saline solution comprising between about 0.1 mg/mL to about 25 mg/mL of the compound of Formula I or a pharmaceutically acceptable salt thereof. Certain preferred pharmaceutical compositions for parenteral administration comprise between about 0.5 mg/mL to about 10 mg/mL of the compound of Formula I or a pharmaceutically acceptable salt thereof in a saline solution which optionally comprises one or more pharmaceutically acceptable additives.

In certain preferred pharmaceutical compositions, the composition comprises between about 25 mg to about 5000 mg or between about 5 mg to about 2500 mg of the compound according to the Formula (I) or an equivalent molar amount of a pharmaceutically acceptable salt thereof. In certain other pharmaceutical compositions of the invention, the composition comprises between about 1 mg to about 1500 mg of the compound according to the Formula (I) or an equivalent molar amount of a pharmaceutically acceptable salt thereof. Yet other pharmaceutical compositions are formulated to comprise about 20 mg, about 30 mg, about 40 mg, about 50 mg, about 60 mg, about 70 mg, about 80 mg, about 90 mg, or about 100 mg of a compound of Formula I or an equivalent molar amount of a pharmaceutically acceptable salt thereof.

In certain methods of treating a patient suffering from or susceptible to cancer, the administration of the compound according to formula I to a patient suffering from or susceptible to cancer decreases tumor size by at least 50% or more preferably by at least about 60%, 70%, 80%, 90% or about 95%. In certain other methods of treating a patient suffering from cancer, the administration of the compound according to formula I to a patient suffering from cancer decreases tumor size by at least 99% or decreases tumor size until no detectable tumor remains.

Certain preferred methods of treating patients suffering from cancer include treatment or prevention of cancer or other tumor disorders in mammalian patients including livestock, companion animals (dogs, cats, horses and the like), primates and humans.

Treatment methods of the invention include in general administration to a patient a therapeutically effective amount of one or more compounds of Formula I. In the instant therapeutic methods, a therapeutically effective amount is sufficient to reduce the size of renal cell carcinoma tumors present in a patient or to eliminate tumors from the patient. Suitable patients include those subjects suffering from a disorder or disease identified herein. Typical patients for treatment in accordance with the invention include mammals, particularly primates, especially humans. Other suitable subjects include domesticated companion animals such as a dog, cat, horse, and the like, or a livestock animal such as cattle, pig, sheep and the like.

Preferred methods of the invention include identifying and/or selecting a subject (e.g. mammal, particularly human) that is suffering from a condition disclosed herein, particularly a subject that is suffering from one or more cancers. A pharmaceutical composition of the invention also may be packaged together with instructions (i.e. written, such as a written sheet) for treatment of a cancer as disclosed herein, e.g. instruction for treatment of a subject that is suffering from cancer.

Compounds of the invention are suitably administered to a subject in a water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc obtained after proper chemical transformation. Also, where an acidic group is present on the compound, a pharmaceutically acceptable salt of an organic or inorganic base can be employed, such as an ammonium salt, or salt of an organic amine, or a salt of an alkali metal or alkaline earth metal such as a potassium, calcium or sodium salt. Specifically suitable pharmaceutically acceptable salts include those formed with a non-toxic cation, preferably an alkali metal cation such as K or Na, an alkaline earth metal cation such as Mg or Ca, another non-toxic metal cation such as Al or Zn or a non-toxic metalloid cation such as $NH_4^+$, piperazinium or 2-hydroxyethylammonium. Certain preferred compounds suitable for use in the methods of the invention are sufficiently water-soluble in neutral form in such a way that they may be delivered without pre-generation of a pharmaceutically acceptable salt.

Compounds suitable for use in the methods of the present invention include any and all different single pure isomers and mixtures of two or more isomers. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers. Preferred enantiomerically enriched compounds have an enantiomeric excess of 50% or more, more preferably the compound has an enantiomeric excess of 60%, 70%, 80%, 90%, 95%, 98%, or 99% or more. Compounds of the invention according to Formula I for use in the methods of the invention can be employed, either alone or in combination with one or more other therapeutic agents, as a pharmaceutical composition in mixture with conventional excipients, i.e., pharmaceutically acceptable organic or inorganic carrier substances suitable for a desired route of administration which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, solutions, preferably oily or aqueous solutions as well as suspensions, emulsions, or implants, including suppositories, are particularly suitable. Ampoules are convenient unit dosages.

For enteral application, particularly suitable are tablets, dragées or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated, including those wherein the active component is protected with differentially degradable coatings, e.g., by microencapsulation, multiple coatings, etc. Tablets, capsules and syrups or other fluids are generally preferred for oral administration.

It should be understood that in addition to the ingredients explicitly mentioned above the formulations of this invention may include other agents conventional in the art with regard to the type of formulation in question, for example, those suitable for oral administration may include flavoring agents.

According to certain embodiments, a compound of Formula I may be administered in combination with other compounds, including for example, chemotherapeutic agents, anti-inflammatory agents, anti-pyretic agents radiosensitizing agents, radioprotective agents, urologic agents, anti-emetic agents, and/or anti-diarrheal agents, for example, cisplatin, carboplatin, docetaxel, paclitaxel, fluorouracil, capecitabine, gemcitabine, irinotecan, topotecan, etoposide, mitomycin, gefitinib, vincristine, vinblastine, doxorubicin, cyclophosphamide, celecoxib, rofecoxib, valdecoxib, ibuprofen, naproxen, ketoprofen, dexamethasone, prednisone, prednisolone, hydrocortisone, acetaminophen, misonidazole, amifostine, tamsulosin, phenazopyridine, ondansetron, granisetron, alosetron, palonosetron, promethazine, prochlorperazine, trimethobenzamide, aprepitant, diphenoxylate with atropine, and/or loperamide. In one preferred embodiment the compound according to Formula I is administered in combination with antiangiogenetic drugs, including for example monoclonal antibodies directed against Vascular Endothelial Growth Factor (VEGF) and Placental Growth Factor (PlGF); and inhibitors of the VEGF and PlGF receptors, including for example bevacizumab, sorafenib, PTK78, SU11248, AG13736, AEE788, and ZD6474. In another embodiment the compound according to Formula I is administered in combination with immunomodulatory drugs, including for example interleukin 2 (IL-2) and Interferon alpha (IFNα). In yet another embodiment the compound according to Formula I is administered in combination with drugs interfering with cellular growth signaling, including for example inhibitors of the mammalian target of rapamycin (mTOR).

In yet other embodiments of the present invention the compounds according to Formula I are chemically bound to molecules that enhance the target selectivity even further by targeting the compounds of Formula I specifically to cancerous cells. Examples of such molecules include (A) polyclonal and monoclonal antibodies directed against markers occurring specifically or in greater numbers on the target cells compared to normal renal tissue, and (B) ligands to receptors occurring specifically or in greater numbers on the target cells compared to normal renal tissue. Such guidance molecules, and techniques for conjugating them to the compounds according to Formula I, are known in the art, and coupling reactions can be performed by the normally skilled artisan without undue experimentation.

The kit of the invention herein comprises at least one pharmaceutically acceptable carrier and 50 to 3,500 mg of a compound according to Formula I, or the equivalent molar amount of a pharmaceutically acceptable salt thereof, as discussed above. In the kit the compound according to Formula I or acceptable salt thereof and the pharmaceutically acceptable carrier are preferably located in separate compartments. The compound according to Formula I is preferably present as a solid. For administration, the compound according to Formula I or pharmaceutically acceptable salt thereof is preferably combined with the carrier so that it is completely or substantially dissolved in the carrier. The kit may comprise between about 100 mg to about 1,500 mg, and most preferably between about 200 mg to about 500 mg, of the compound according to Formula I or an equivalent amount of the pharmaceutically acceptable salt thereof.

The foregoing description of the invention is merely illustrative thereof, and it is understood that variations and modifications can be effected without departing from the spirit or scope of the invention as set forth in the following claims. Each of the documents referred to herein are incorporated by reference into the disclosure of the application.

EXAMPLES

Example 1

Extraction and Isolation of Orellanine from *Cortinarius* Mushrooms

A. Polar method: 2 g of dried *Cortinarius* mushroom were powdered and then extracted with 50% methanol for 24 h at 25° C. The mixture was centrifuged, and the supernatant removed to a final volume of 5 ml. Upon repeated addition of 5 vol of cold methanol, a precipitate formed which was discarded until a clear solution formed. The solvent was evaporated, the residue dissolved in water and apolar substances removed by extraction with petroleum ether. The polar phase was loaded onto a Sephadex column and eluted with 50% ethanol. The resulting fractions were chromatographed on thin layer cellulose, eluting with butanol:acetic acid:water (3:1:1). Orellanin was identified as a fluorescent band at Rf 0.68.

B. Apolar method: 4 g of powdered *Cortinarius* mushroom were refluxed for 24 h in diethyl ether, and the solvent was discarded. The residue was refluxed in methanol followed by solvent evaporation and washing with 20 ml of water (6 h, 4° C.). They were then dissolved in 50% aqueous ethanol (pH 7.0). The mixture was loaded onto a Sephadex column and eluted with 50% ethanol. The resulting fractions were chromatographed on thin layer cellulose, eluating with butanol: acetic acid:water (3:1:1). Orellanin was identified as a fluorescent band at Rf 0.68.

Example 2

Synthesis of Orellanine

Orellanine was synthesized from commercially available 3-hydroxypyridine essentially as described by others. (Tiecco M, Tingoli M, Testaferri L, Chianelli D and Wenkert E: Total synthesis of orellanine, the lethal toxin of *Cortinarius orellanus* Fries Mushroom. *Tetrahedron* 42, 1475-1485 (1986))

Example 3

Orellanine has a Specific Toxic Effect on Human Renal Cell Carcinoma Cells in vitro Background and Methodology.

Cells harvested from 5 different human renal cell carcinomas (SKRC-52, 786-0, SKRC-17, SKRC-7 and SKRC-21), representing both mother tumors and metastatic growths, were cultured under standard conditions. When approximately 70% confluent and in rapid growth, the cells were exposed to medium containing Orellanine (400 µM) for 24 h. Then the medium was changed back to regular, complete medium and the cells were observed for another six days.

Results and Comments.

Figure 1:
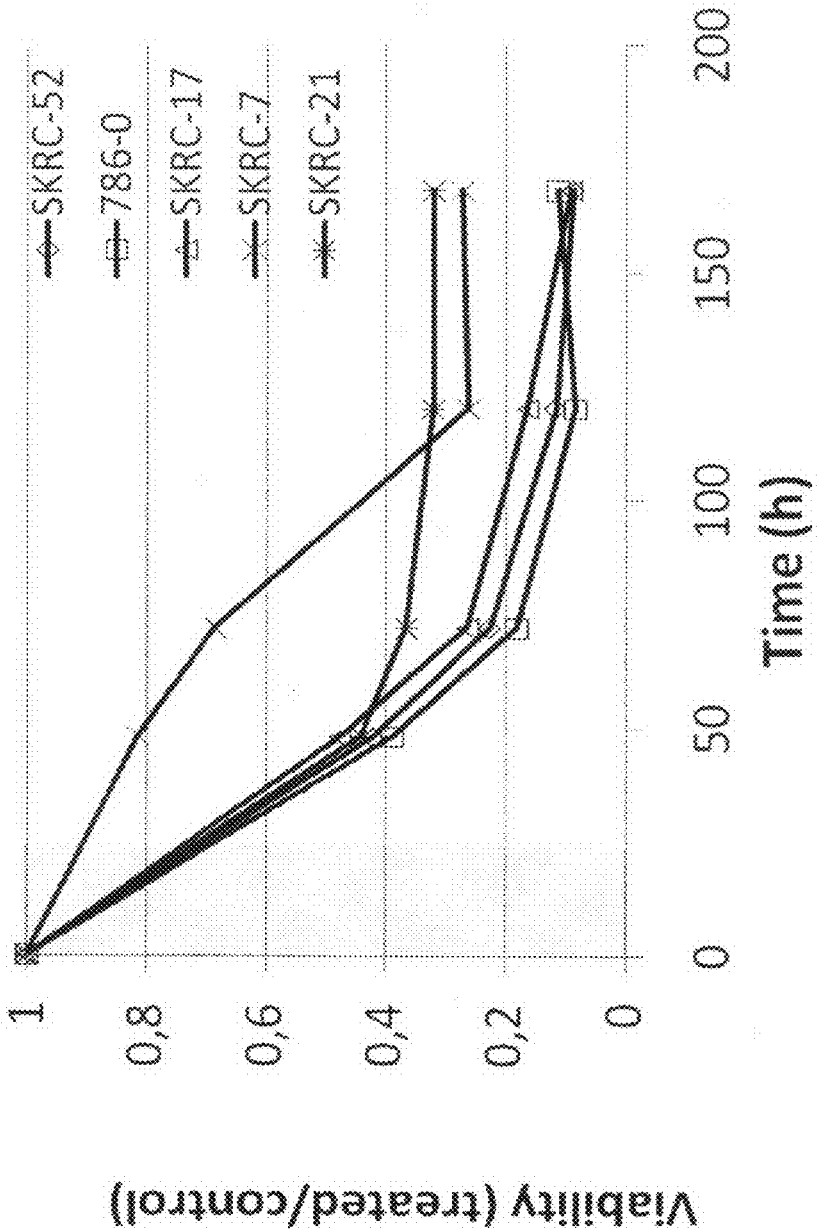
FIG. 1: Observation of the viability of cells from 5 different human renal cell carcinomas (primary tumors and metastases) during 7 days following 24 h of exposure to 400 µM orellanine (100 µg/ml culture medium. Viability is calculated by dividing the number of living cells in treated samples by the number of living cells in control samples (n=6). The gray area in the graph represents the period of orellanine incubation (24 h). The following days the cells were cultured in orellanine-free complete culture medium. The medium was changed at each viability measurement.
Figure 2:
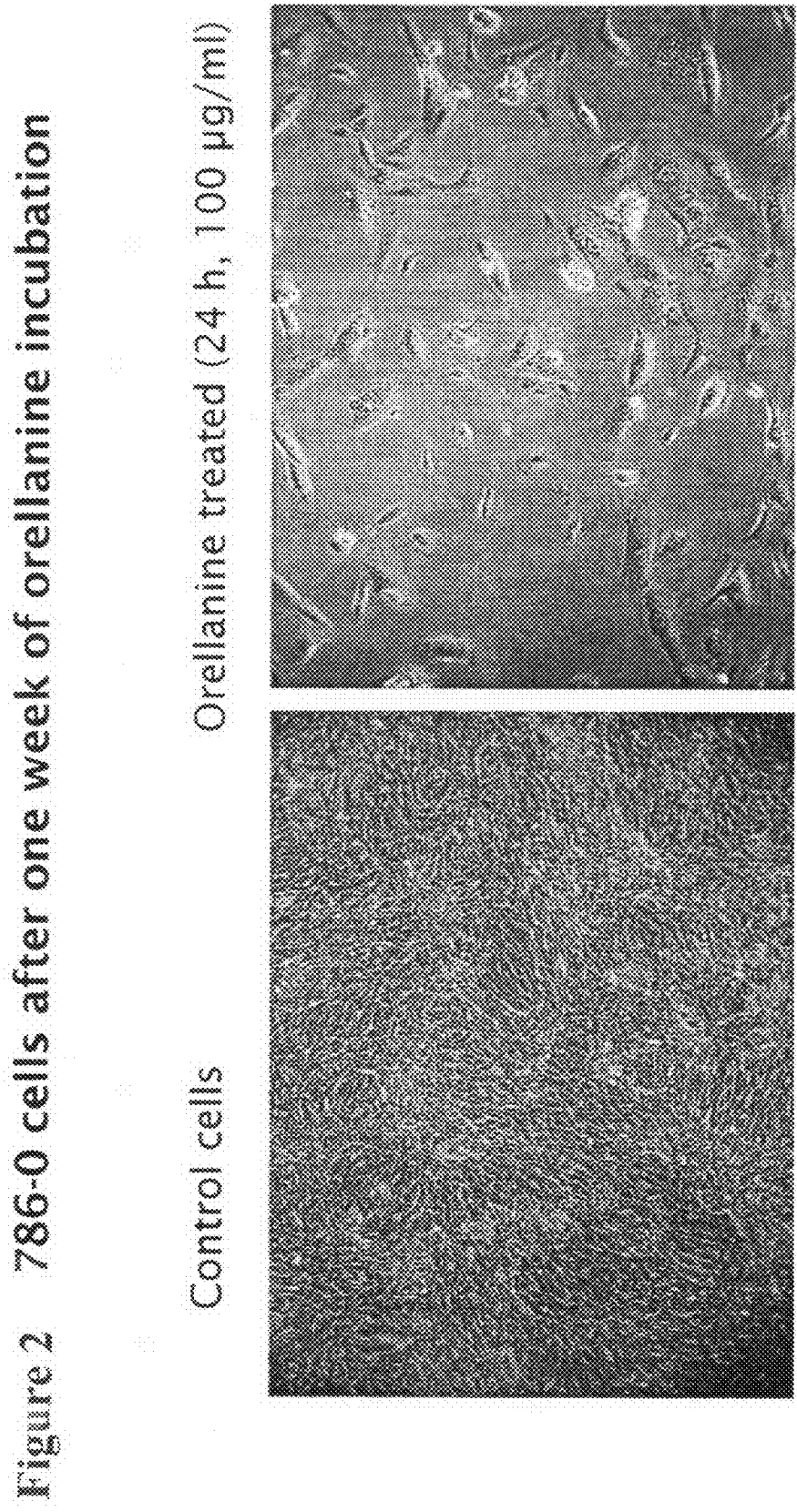
FIG. 2: Orellanine toxicity towards human renal carcinoma cells (strain 786-0) one week after orellanine incubation according to the same parameters as in FIG. 1. The left micrograph shows cells which have been exposed to vehicle, and the right micrograph shows cells exposed to 400 µM orellanine for 24 h. Both pictures were taken with the same magnification, and one week after incubation with orellanine/vehicle.

The effect of the described Orellanine treatment of the cells is illustrated in FIG. 1. It is evident from the figure that Orellanine was highly toxic to all the tested cell types. Moreover, the toxicity was not affected by removal of Orellanine from the culture medium after the initial exposure. This suggests that Orellanine accumulates in the cells and remains there even when no extracellular Orellanine is present. FIG. 2 shows the appearance of the cells before and one week after 24 h of Orellanine exposure.

Example 4

Dose-response Effect of Orellanine

Background and Methodology

Cells harvested from 2 different human renal cell carcinomas (SKRC-7, 786-0), representing both mother tumors and metastatic growths, were cultured under standard conditions. When approximately 70% confluent and in rapid growth, the cells were exposed to medium containing different concentrations of Orellanine (400 µM) for 24 h. Then the medium was changed back to regular, complete medium and the cells were observed for another six days.

Results and Comments

Figure 3:
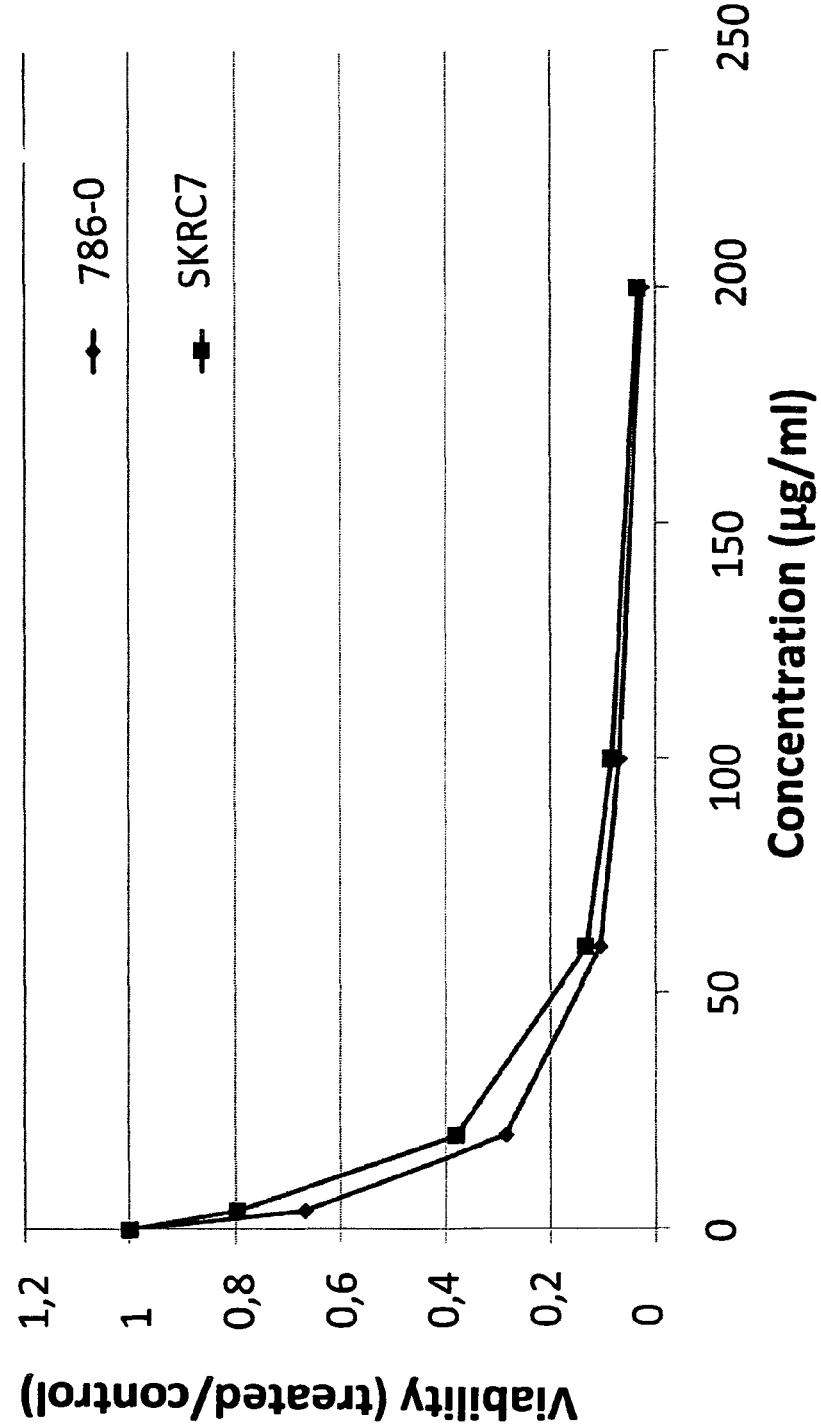
FIG. 3: Dose/response effect of different concentrations of Orellanine in the culture medium of human renal cell carcinomas (786-0 and SKRC7). A clear correlation between orellanine dose and cell death is seen in the concentration interval 5-200 µg/ml.
Figure 4:
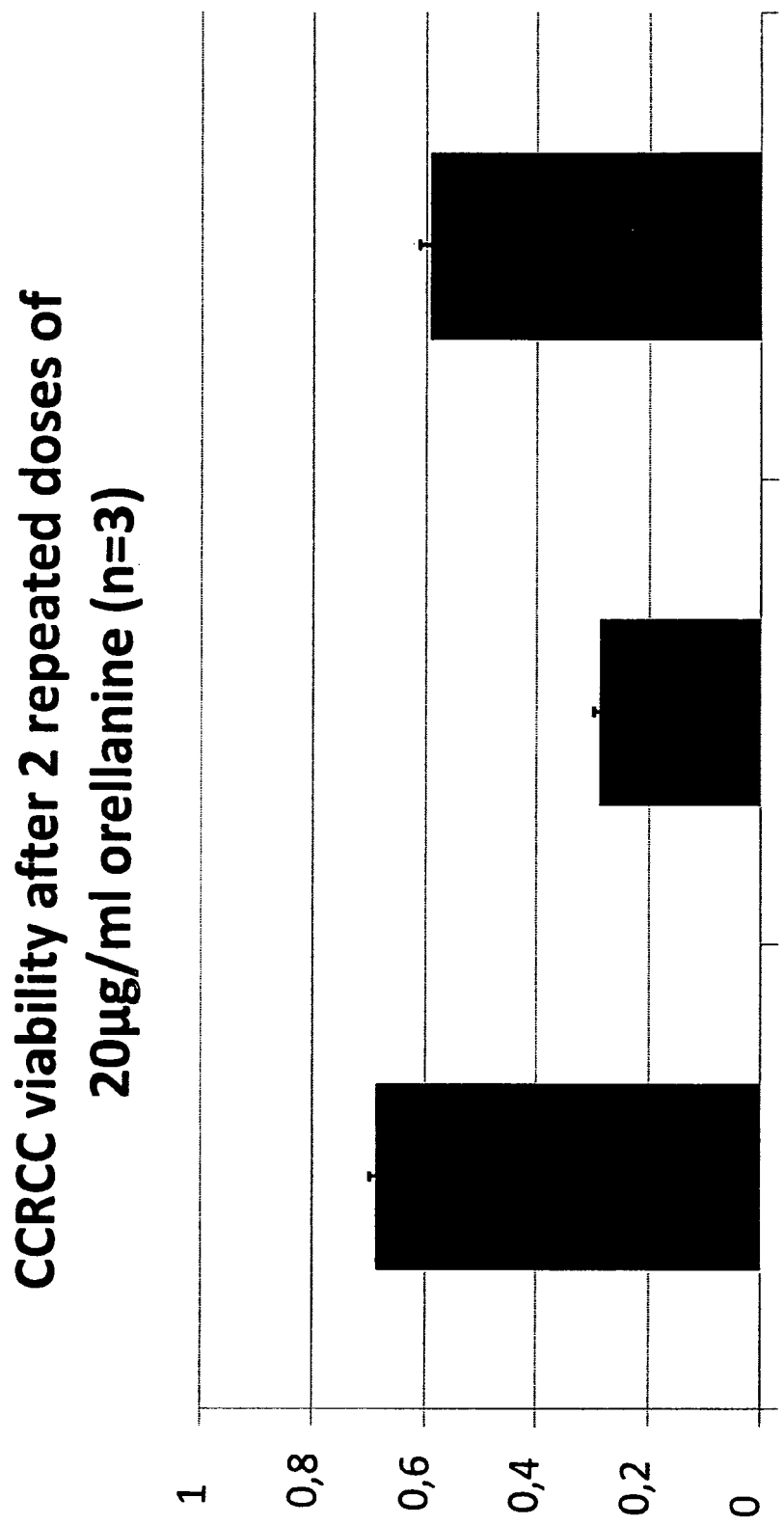
FIG. 4: Effect of repeated administration of a lower dose of orellanine. Administration of a second dose at the lower end of the dose/response interval (20 µg/ml) 24 h after the first dose led to a strong decrease in the number of viable cells, whereas administration of the second dos at 72 h had a considerably smaller, but still significant, effect. The first case is equivalent to a prolonged exposure of the cells (48 h), whereas the cells in the second case have been allowed to recover in orellanine-free medium for two days between the doses. Viability was measured 96 h after addition of the first orellanine dose.

As seen in FIG. 3, there is a clear correlation between the exposure concentration and the fraction of cells that die. The dose response interval for a single 24 h-exposure of orellanin is between approximately 5 µg/ml and 200 µg/l.

Example 5

Effects of Repeated Administration of Smaller Doses of Orellanine

Background and Methodology

Cells harvested from the human renal cell carcinoma 786-0 were cultured under standard conditions. When approximately 70% confluent and in rapid growth, the cells were exposed to medium containing a low concentration of Orellanine (20 µg/ml) for 24 h. Then the medium was changed to new medium either containing 20 µg/ml orellanine for 24 h (middle bar) or back to regular, complete medium for 48 h, followed by another 24 h in the presence of 20 µg/ml orellanine (rightmost bar).

Results and Comments

Repeated exposure to orellanine, even in doses at the lower limit of the single exposure response interval, produced further, marked toxic effects on renal cancer cells.

Example 6

Effects of Orellanine on Other Cell Types

Background and Methodology

Cell lines and primary cells originated from numerous human tissues (tubular epithelium, podocytes and mesangial cells from renal tissue, fibroblasts, macrophages, aortic endothelium, microvascular endothelium and umbilical chord endothelium, intestinal epithelium (duodenal, jejunal, ileal and colonic) and chondrocytes) were cultured under standard conditions. When approximately 70% confluent and in stable growth, the cells were exposed for 24 h to medium containing orellanine in concentrations selected in order to achieve a dose response. Then the medium was changed back to regular, complete medium and the cells were observed for another six days, followed by viability determination. To compensate for any growth retarding effects caused by dilution of the culture medium by the large volume of orellanine solution added, all cells were supplemented with equal volumes of orellanine buffer.

Results and Comments

None of the tested cell types exhibited any effects on viability when exposed for orellanine according to Example 4 in concentrations up to 1,000 µg/ml which was the highest achievable concentration.

Example 7

Orellanin Induces Growth-arrest by Halting the Cell Cycle

Background and Methodology

Renal cancer cells, cultured essentially as described in Example 3, were treated with orellanin (100 µg/ml culture medium) for 24 h. During this period cells were harvested after 0, 2, 6 and 24 h exposure. Western blots were performed on the harvested material with antibodies directed against A) the kinase inhibitor p21, B) phosphorylated retinoblastoma protein (a growth stimulating factor), and C) the cdc2 protein which allows the cell to proceed into the M-phase of the cell cycle where the cell divides.

Results and Comments

Figure 5:
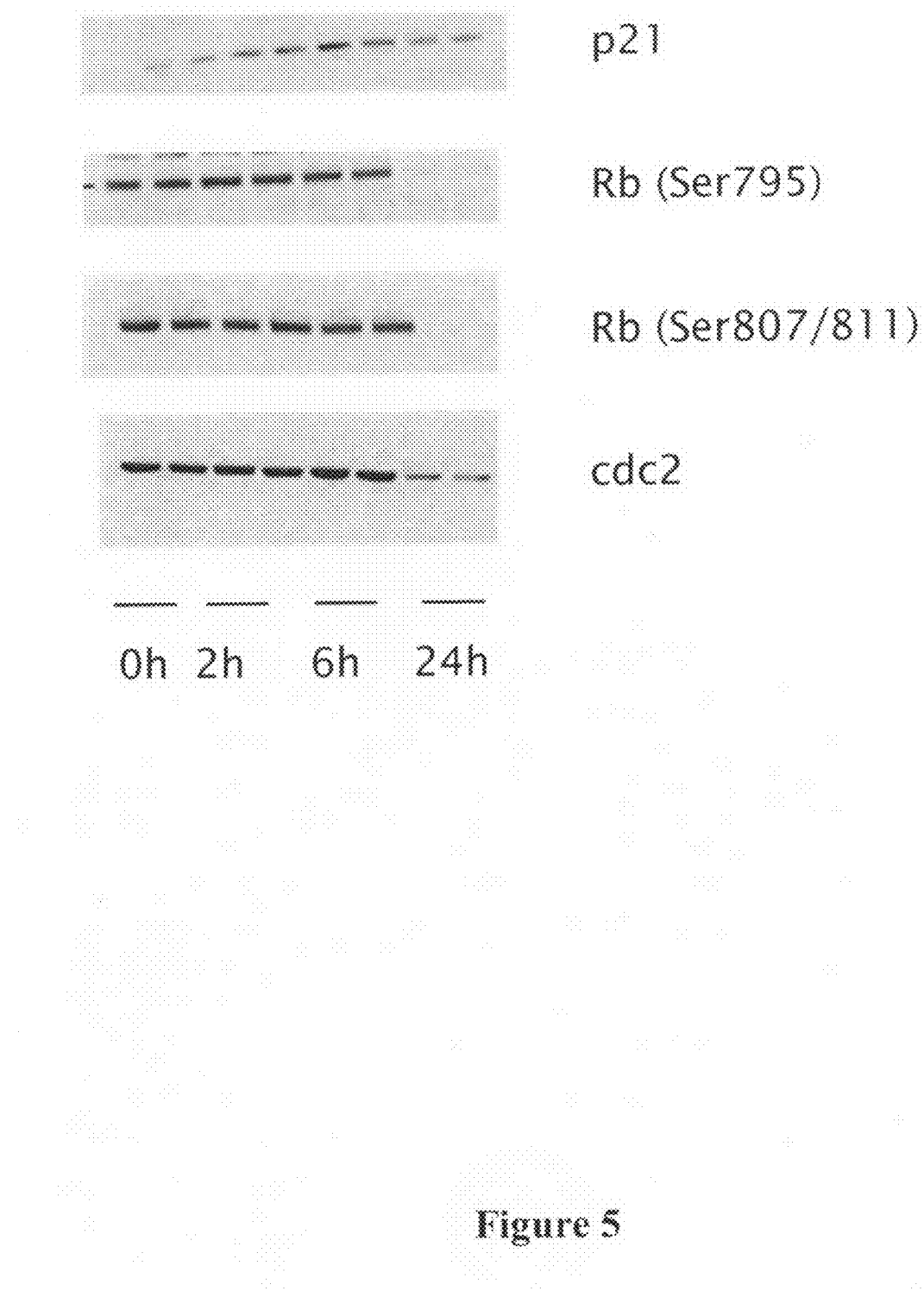
FIG. 5: Effects of orellanine on the cell cycle in renal cell carcinoma (786-0 and SKRC-52) (Western Blot). Protein levels of the cell cycle inhibitor p21 are gradually up-regulated with a maximum at 6 h incubation. After 24 h, the cell cycle-stimulating phosphorylated form of the retinoblastoma protein (Rb) has disappeared (two different phosphorylation sites shown). Both these effects converge to halt the cell cycle at the check point G1/S. Simultaneously, loss of the stimulating factor cdc2 arrests the cell cycle at the check point G2/M, preventing initiation of cell division.

The effects of orellanine exposure on the protein expression of p21, the retinoblastoma protein and cdc2 are shown in FIG. 5 The intracellular levels of the cell cycle inhibitor p21 are increased with a maximum around 6 h, while the cell cycle stimulating phosphorylated forms of the retinoblastoma protein are completely lacking at the 24 h measurement. In a similar fashion the cdc2 protein, which allows the cell to enter the cell division phase, is dramatically down-regulated at 24 h. This clearly indicates that orellanine has a profound inhibitory effect on the cell cycle, which is exerted at least two important check points.

Example 8

Figure 6:
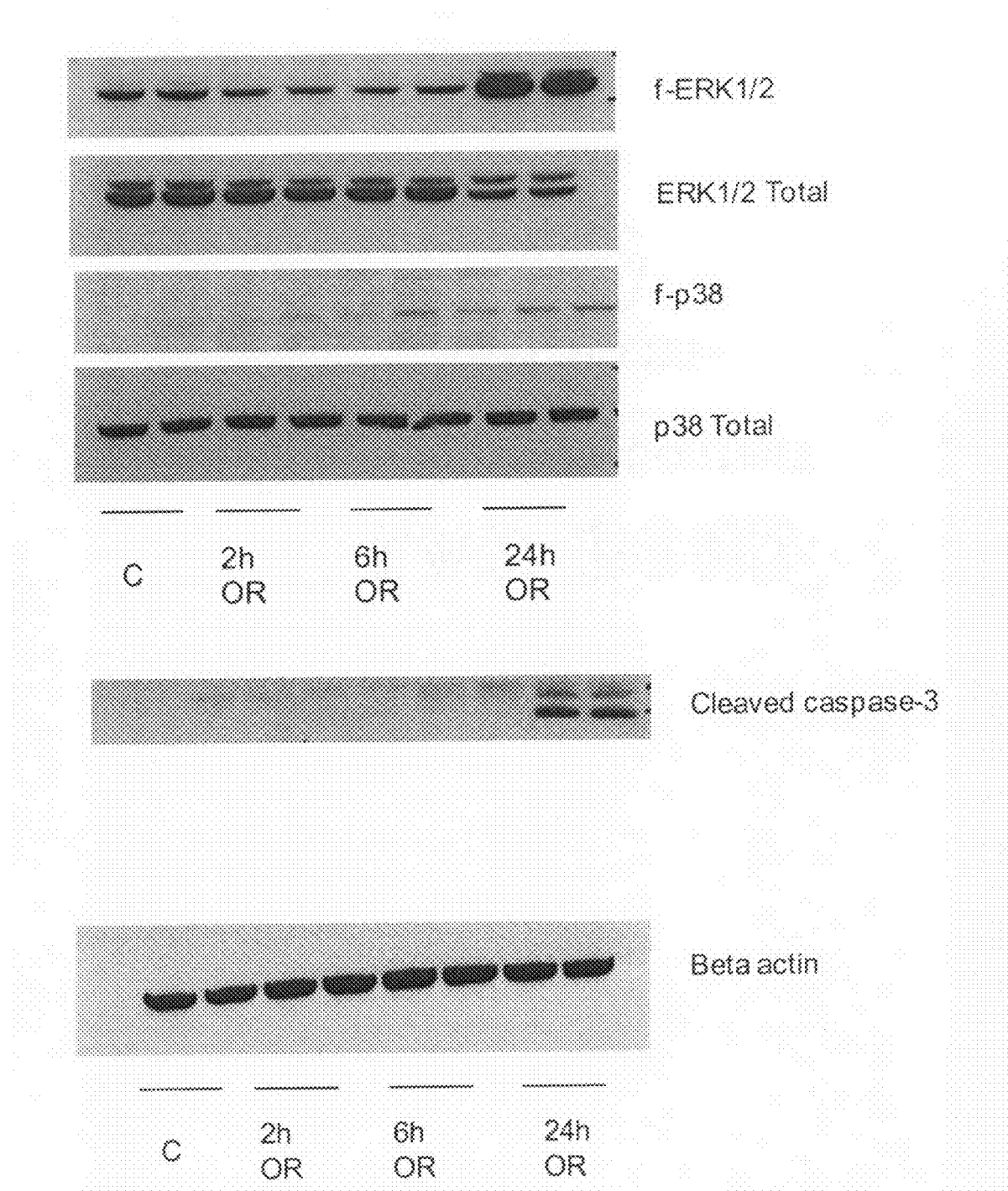
FIG. 6: Induction of apoptosis by orellanine in renal carcinoma cells (786-0): Protein effects. The apoptotic p38 pathway was strongly upregulated (f-p38) after Orellanine exposure (OR), and apoptosis was detected in the form of cleaved caspase 3. The strong up-regulation of ERK1/2 after 24 h (f-ERK1/2) is interpreted as an attempt of the cells to counteract the apoptotic influences of Orellanine.

Orellanine Increases Activity of Several Apoptosis-inducing Pathways, Causing Cancer Cell Death Background and Methodology Renal cancer cells were cultured and exposed to orellanine according to Example 7 and harvested at various times up to 24 h. The p38 MAPK system, the p53 system, Fas Ligand, Tumor Necrosis Factor alpha (TNF) and cleaved caspase 3 are key factors in apoptotic pathways leading to cell death. Western blotting was used to determine intracellular levels of A) p38, B) cleaved caspase 3, and C) the proliferative factor phosphorylated ERK 1/2. Quantitative PCR was used to determine the mRNA expression of D) p53 upregulated modulator of apoptosis (PUMA) which mediates virtually all apoptotic effects of the p53 pathway, E) Fas ligand and F) TNF Results and Comments The results are summarized in FIGS. 6-8. There was a steady increase of phosphorylated (activated) p38 throughout the 24-h observation period, increasing the apoptotic signal strength in the cell (FIG. 6). (The simultaneous up-regulation of the growth stimulator phosphorylated ERK 1/2 is interpreted by the inventors as an attempt by the cell to "outgrow" the apoptotic influence of orellanine.)

On the mRNA level, the extreme up-regulation of PUMA and the death receptor ligands FasL and TNF constitutes a strong apoptotic stimulus (FIG. 7). Finally, the amount of cleaved caspase-3, a main effector of apoptosis, was dramatically increased 24 h after exposure to orellanine (FIG. 6).

Together with the images of increasingly apoptotic cells presented in FIG. 8, the above results clearly indicate apoptosis as the principal mode of action of orellanine in renal cancer cells.

Example 9

Orellanine Eradicates Human Renal Cell Carcinomas Growing in Athymic Rats

Background and Methodology

Athymic, T cell-deficient rats (RNU, Charles River Laboratories, FRG) are used as a system for in vivo-growth of human renal cell carcinomas. The absence of a T cell-based immune defense in these animals makes them tolerant towards xenografts. One week after arrival in the animal facility 10 animals receive an X-irradiation dosis of 5 Gy in order to suppress also their B cell-mediated response.

The next day, all animals are equipped with an indwelling catheter for peritoneal dialysis (PD). PD treatment will replace the renal function that is lost as a side-effect upon administration of orellanine.

One day later, 5 animals are inoculated subcutaneously in the shoulder region with approximately $10 \times 10^6$ human renal carcinoma cells (SKRC-52). The 5 remaining animals receive the same amount of cells by intravenous injection. In the subcutaneous group localized tumors, $1 \times 1 \times 2$ cm, are palpable under the animals' skin after 2-4 weeks. At this point 2 animals (controls) in each group are injected i.p. with physiological saline solution and the remaining 3 animals receive 10 mg orellanine/kg b.w. i.p.

Results and Comments

Two weeks after the first injection of saline/orellanine, the tumors of the control animals in the subcutaneous group have approximately doubled in size, while the tumors in the animals injected with Orellanine have shrunk to less than 25% of the size recorded at the time of injection. At this point another dose of 5 mg Orellanine/kg b.w. is injected into the tumor site of the 3 animals in the subcutaneous group that previously have received Orellanine, and the control animals receive 10 mg Orellanine/kg b.w. into the tumor site. After another 2 weeks no signs of the tumors are evident in the animals injected twice with Orellanine, and the tumor size in the former control animals are reduced by more than 75%.

One and two weeks after the first saline/orellanine injection, the 5 animals in the intravenous group receive i.v. injections of 5 mg/kg orellanine or saline, respectively. Another week later, the animals are terminated and their abdominal and thorax cavities are scanned for tumor growth. Estimation of tumor mass shows that the orellanine-treated animals have less than 10% of the tumor burden of the control animals.

This clearly demonstrates the tumor-killing activity of Orellanine in an in vivo-system.

Example 10

Safety of i.v. Orellanin During Long Term Treatment in Pigs and Dogs 5 pigs of the Göttingen minipig strain and 5 dogs of mixed breeding (body weight 10-15 kg) are set up for hemodialysis using equipment designed for children and infants. The animals receive initial doses of 10 mg orellanine/kg b.w. 24 h later, the animals are subjected to a dialysis session of approximately 3 h. After dialysis, the animals are injected with 5 mg orellanine/kg b.w. The dialysis/reinjection procedure is repeated 3 times a week (Monday, Wednesday, Friday) for 8 weeks. Once a week an assessment of the animals' general condition is made. At the end of the experiment all animals are terminated, and specimens for histopathological evaluation are taken from heart, lung, kidney, liver, spleen, small intestine, large intestine, brain, muscle and skin.

Behavior and general condition of the animals remain normal throughout the experimental period. Histopathological examination reveals no tissue damage with the exception of the kidneys where there is widespread tubular damage leading to complete renal failure.

The results show that long term treatment with high doses of orellanine is safe from the renal cancer patient's point-of-view, with negligible side-effects in non-renal tissue.

Example 11

Treatment of a Human Patient, Suffering from Advanced Renal Cell Carcinoma, with Orellanine A patient in need of treatment for a renal carcinoma is given a series of 10 daily intravenous injections of Orellanine. The initial tumor burden of the patient is determined to be approximately 2 kg. Based on this value, the appropriate daily dose is determined to 280 mg (4 mg/kg at b.w. 70 kg). Before the first injection, the patient is prepared for hemodialysis or peritoneal dialysis since the Orellanine treatment will inevitably destroy healthy renal epithelial tissue along with the killing of the cancer cells, thus leaving the patient without renal function. Two hours after each injection, hemodialysis is started and maintained for 2 hours. This procedure, with repeated administration of smaller amounts of orellanine, has the benefit of effecting a gradual buildup of orellanine to lethal levels in the tumor tissue, which actively takes up the substance, while extracellular concentrations of the toxin are kept below levels that might cause side-effects. Optionally, if the disease is unilateral, the unaffected kidney may be surgically removed and preserved during the treatment, and reimplantation attempted after conclusion of the treatment. The progress of the patient is monitored for one month, whereafter additional serial administrations of Orellanine are given as needed to inhibit growth of the renal carcinoma. During the treatment, the mass of tumor tissue in the patient is decreasing, and at the conclusion of the treatment the renal cancer is completely eradicated, demonstrating the efficacy of orellanine against renal clear cell carcinoma.

What is claimed is:

1. A method for treating a patient suffering from renal cell carcinoma, comprising administering to the patient a compound according to the Formula I:

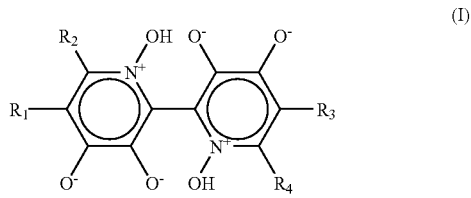

wherein
R1, R2, R3 and/or R4 are selected from the group consisting of hydrogen, amino, mercapto, carboxy, phosphate and halo, $C_1$-$C_6$ alkyl, $C_1$-$C_6$ alkenyl, $C_1$-$C_6$ alkynyl, $C_1$-$C_6$ alkanol, $C_1$-$C_6$ alkenol, $C_1$-$C_6$ alkoxy, and $C_1$-$C_6$ alkenoxy, and wherein $C_1$-$C_6$ alkyl, $C_1$-$C_6$ alkenyl, $C_1$-$C_6$ alkynyl, $C_1$-$C_6$ alkanol, $C_1$-$C_6$ alkenol, $C_1$-$C_6$ alkoxy, and $C_1$-$C_6$ alkenoxy may be further substituted with groups selected from the group consisting of amino, mercapto, carboxy, phosphate and halo, and a pharmaceutically acceptable salt thereof, wherein the treatment results in a reduction in tumor size.

2. The method of claim 1, wherein $R_1$, $R_2$, $R_3$ and $R_4$ are hydrogen.

3. The method of claim 1, wherein the compound of Formula I is a pharmaceutically acceptable salt.

4. The method of claim 1, wherein the compound is administered as a single dose of about 1 mg/kg to about 100 mg/kg.

5. The method of claim 1, wherein the compound is administered in two or more doses, wherein each dose comprises between about 1 mg/kg and about 20 mg/kg of the compound.

6. The method of claim 2, wherein the compound is administered in two or more doses, wherein each dose comprises between about 1 mg/kg and about 20 mg/kg of the compound.

7. The method of claim 3, wherein the compound is administered in two or more doses, wherein each dose comprises between about 1 mg/kg and about 20 mg/kg of the compound.

8. The method of claim 5, wherein sequential doses are administered between two and seven days apart.

9. The method of claim 6, wherein sequential doses are administered between two and seven days apart.

10. The method of claim 7, wherein sequential doses are administered between two and seven days apart.

11. The method of claim 1, wherein the compound is administered daily.

12. The method of claim 2, wherein the compound is administered daily.

13. The method of claim 3, wherein the compound is administered daily.

14. The method of claim 1, wherein the compound is administered intravenously, subcutaneously, or intraperitoneally.

* * * * *